US008217220B2

(12) United States Patent
Berland et al.

(10) Patent No.: US 8,217,220 B2
(45) Date of Patent: Jul. 10, 2012

(54) ABSORBENT ARTICLE COMPRISING A THIN FILM INCLUDING AN ACTIVE AGENT

(75) Inventors: Carolyn Berland, Mölndal (SE); Shabira Abbas, Göteborg (SE)

(73) Assignee: SCA Hygiene Products AB, Göteborg (SE)

(*) Notice: Subject to any disclaimer, the term of this patent is extended or adjusted under 35 U.S.C. 154(b) by 131 days.

(21) Appl. No.: 11/992,644

(22) PCT Filed: Oct. 5, 2005

(86) PCT No.: PCT/EP2005/010737
§ 371 (c)(1),
(2), (4) Date: Mar. 27, 2008

(87) PCT Pub. No.: WO2007/038966
PCT Pub. Date: Apr. 12, 2007

(65) Prior Publication Data
US 2009/0275906 A1 Nov. 5, 2009

(51) Int. Cl.
A61F 13/15 (2006.01)
A61F 13/20 (2006.01)
(52) U.S. Cl. .................. 604/367; 604/375; 604/378
(58) Field of Classification Search ........... 604/367–375
See application file for complete search history.

(56) References Cited

U.S. PATENT DOCUMENTS

| 3,489,148 A | 1/1970 | Duncan et al. |
| 3,704,034 A | 11/1972 | Shire et al. |
| 3,998,690 A | 12/1976 | Lyness et al. |
| 4,351,784 A | 9/1982 | Thomas et al. |
| 4,449,977 A * | 5/1984 | Korpman ............... 604/366 |
| 4,695,278 A | 9/1987 | Lawson |
| 4,743,494 A | 5/1988 | Komatsu et al. |
| 4,992,326 A | 2/1991 | Dabi |
| 5,198,224 A * | 3/1993 | Ono et al. .............. 424/450 |
| 5,554,147 A | 9/1996 | Batich et al. |
| 5,558,655 A | 9/1996 | Jezzi et al. |
| 5,607,417 A | 3/1997 | Batich et al. |
| 5,658,582 A | 8/1997 | Dorigatti et al. |
| 5,700,559 A | 12/1997 | Sheu et al. |
| 5,807,636 A | 9/1998 | Sheu et al. |
| 5,837,377 A | 11/1998 | Sheu et al. |
| 5,885,753 A | 3/1999 | Crooks et al. |
| 6,428,811 B1 | 8/2002 | West et al. |
| 6,861,103 B2 | 3/2005 | Chang et al. |
| 2004/0047979 A1 | 3/2004 | Qiu et al. |
| 2004/0122388 A1 | 6/2004 | McCormack et al. |
| 2004/0137039 A1 | 7/2004 | Sukhishvili et al. |
| 2005/0069950 A1 | 3/2005 | Haynie |

FOREIGN PATENT DOCUMENTS

| CN | 1031545 A | 3/1989 |
| DE | 33 09 530 | 10/1984 |
| DE | 38 34 797 A1 | 4/1990 |
| DE | 41 36 540 | 5/1992 |
| EP | 0 348 979 | 1/1990 |
| EP | 0 456 467 | 11/1991 |
| EP | 0 483 858 | 5/1992 |
| EP | 0 510 619 | 10/1992 |
| EP | 0 631 768 | 1/1995 |
| EP | 0 640 330 | 3/1995 |
| EP | 0 878 481 | 11/1998 |
| JP | 2005-528971 A | 9/2005 |
| WO | WO 91/11977 | 8/1991 |
| WO | WO 91/12029 | 8/1991 |
| WO | WO 91/12030 | 8/1991 |
| WO | WO 94/28568 | 12/1994 |
| WO | WO 95/01147 | 1/1995 |
| WO | WO 96/16681 | 6/1996 |
| WO | WO 96/16682 | 6/1996 |
| WO | WO 97/04819 | 2/1997 |
| WO | WO 97/05909 | 2/1997 |
| WO | WO 97/46188 | 12/1997 |
| WO | WO 97/46190 | 12/1997 |
| WO | WO 97/46192 | 12/1997 |
| WO | WO 97/46193 | 12/1997 |
| WO | WO 97/46195 | 12/1997 |
| WO | WO 97/46196 | 12/1997 |

(Continued)

OTHER PUBLICATIONS

International Search Report and Written Opinion issued Aug. 8, 2006 in corresponding PCT/EP2005/010737.
Lee "Constant-Rate Drug Release from Novel Anionic Gel Beads with Transient Composite Structure," *Journal of Pharmaceutical Sciences*, American Pharmaceutical Association, Washington, US, 82(9):964-967 (Sep. 1, 1993).
Qiu et al., "Studies on the Drug Release Properties of Polysaccharide Multilayers Encapsulated Ibuprofen Microparticles," *Langmuir* 17:5375-5380 (2001).
International Preliminary Report on Patentability issued Feb. 22, 2008 in corresponding PCT/EP2005/010737.

(Continued)

*Primary Examiner* — Michele M Kidwell
(74) *Attorney, Agent, or Firm* — Buchanan Ingersoll & Rooney PC

(57) ABSTRACT

An absorbent article such as a diaper, panty diaper, panty liner, sanitary napkin or incontinence device, wherein at least one part of the absorbent article carries a film having at least one monomolecular layer of a polymer having a functional group and an active agent, in particular to an absorbent article wherein the film is obtainable by layer-by-layer deposition of at least a first polymer having a first functional group and a second polymer having a second functional group capable of interacting with the first functional group. Moreover, the use of a film obtainable by the layer-by-layer deposition of at least one first polymer having a first functional group and a second polymer having a second functional group capable of interacting with the first functional group for releasing an active agent contained in the film upon wetting of the film by body fluids. Preferably the first polymer having a first functional group is a polycationic polymer and the second polymer having a second functional group is a polyanionic polymer.

23 Claims, No Drawings

FOREIGN PATENT DOCUMENTS

| | | |
|---|---|---|
| WO | WO 98/18330 | 5/1998 |
| WO | WO 99/01099 | 1/1999 |
| WO | WO 99/22684 | 5/1999 |
| WO | WO 99/45973 | 9/1999 |
| WO | WO 99/45974 | 9/1999 |
| WO | WO 99/45976 | 9/1999 |
| WO | WO 00/32702 | 6/2000 |
| WO | WO 00/35502 | 6/2000 |
| WO | WO 00/63115 | 10/2000 |
| WO | WO 00/64500 | 11/2000 |
| WO | WO 00/64501 | 11/2000 |
| WO | WO 00/64502 | 11/2000 |
| WO | WO 00/64503 | 11/2000 |
| WO | WO 01/15649 | 3/2001 |
| WO | WO 01/17357 | 3/2001 |
| WO | WO 02/056841 | 7/2002 |
| WO | WO 03/103854 A | 12/2003 |
| WO | WO 03/105916 A1 | 12/2003 |
| WO | WO 2004/007677 | 1/2004 |
| WO | WO 2004/060649 A1 | 4/2004 |
| WO | WO 2004/056403 A2 | 7/2004 |
| WO | WO 2004/071677 | 8/2004 |
| WO | WO 2005/013906 | 2/2005 |
| WO | WO 2005/023536 | 3/2005 |
| WO | WO 2005/032512 A | 4/2005 |
| WO | WO 2005/058199 A | 6/2005 |

OTHER PUBLICATIONS

Antipov et al., "Sustained Release Properties of Polyelectrolyte Multilayer Capsules" J. Phys. Chem. B, 2001, vol. 105, pp. 2281-2284.

Chung et al., "Methods of Loading and Releasing Low Molecular Weight Cationic Molecules in Weak Polyelectrolyte Multilayer Films" Langmuir, 2002, vol. 18, pp. 1176-1183.

Decher et al., "Multilayer Thin Films" Sequential Assembly of Nanocomposite Materials, Wiley VCH, 2003, 13 pages.

Freemantle, "Polyelectrolyte Multilayers" Thin-Film Properties can be Finely Tuned Through Layer-by-Layer Assembly, Science & Technology, 2002, pp. 44-48.

Joly et al., "Multilayer Nanoreactors for Metallic and Semiconducting Particles" Langmuir, 2000, vol. 16, pp. 1354-1359.

Wang et al., "Polyelectrolyte Multilayer Nanoreactors for Preparing Silver Nanoparticle Composites: Controlling Metal Concentration and Nanoparticle Size" Langmuir, 2002, vol. 18, pp. 3370-3375.

First Office Action issued in the corresponding Chinese Patent Application No. 200580051760.4 dated Mar. 30, 2010 and stamped Apr. 1, 2010 (and English-language translation thereof).

A Notice of Reasons for Rejection issued Nov. 2, 2010, in corresponding Japanese Patent Application No. 2008-533875.

\* cited by examiner

ABSORBENT ARTICLE COMPRISING A THIN FILM INCLUDING AN ACTIVE AGENT

The present disclosure relates to an absorbent article such as a diaper, panty diaper, panty liner, sanitary napkin, incontinence device or the like wherein one part thereof includes an active agent. The present disclosure relates in particular to such an absorbent article wherein controlled release of the active agent is effected by a nanoscalar film which is preferably obtained by layer-by-layer deposition of at least two polymers having interacting functionalities.

TECHNICAL BACKGROUND

It is often desirable to provide absorbent articles of the above-mentioned type with functions going beyond their capacity to absorb and store body fluids such as urine or menstrual fluids. These functions involve for instance a skin care effect or the suppression or prevention of unpleasant odours.

Existing absorbent articles that show these additional functions comprise active agents, which are either loosely bound to a diaper part or embedded in a matrix being typically of lotion type (see for instance WO 96/16682) or polymer type. Loosely bound active agents suffer from the disadvantage that they are too easily rubbed off or washed off under body motion or with the first gush of urine. This may also occur if the active agent is fixed in a lotion matrix. Polymer systems, on the other hand, are often not capable of releasing active agents specifically when these are needed, that is upon contact with body fluids. Moreover, relatively high amounts of polymers or lotions are needed for an efficient embedding of the active agent. Polymers and lotions can also adversely affect the properties of the underlying substrate such as flexibility, softness, absorbency, hydrophilicity, etc.

Moreover, nanoscalar films of self-assembling polymers are known from various technical fields and have attracted considerable interest over the last years. These nanoscalar films are typically formed by the alternate deposition of monomolecular layers of two polymers having functional groups capable of interacting with each other. A great deal of these studies has been conducted with the layer-by-layer deposition (also abbreviated as LBL deposition) of cationic and anionic polymers based on the reversal of the surface charge after each deposition, one of the best-examined systems being poly(styrene sulfonate)/(polyallylamine hydrochloride)(PSS/PAH).

U.S. 2005/0069950 A1 discloses a method for the nanofabrication of thin films, coatings and microcapsules based on suitable design of oligopeptides. Drug delivery is discussed in connection with microcapsules. Moreover, disposable diapers are mentioned as one among many possible uses for peptides designed according to this documents. More concretely described are biomedical applications.

U.S. Pat. No. 5,807,636, U.S. Pat. No. 5,700,559 and U.S. Pat. No. 5,837,377 relate to a hydrophilic article for use in aqueous environments including a substrate, an ionic polymeric layer on said substrate and a disordered polyelectrolyte coating ionically bonded to said polymeric layer. Diapers and other liners are mentioned as one among many potential applications of this teaching.

WO 2005/058199 relates to an electrostatically self-assembled antimicrobial coating for medical applications, in particular wound dressings.

WO 00/32702 describes for instance a paper or nonwoven product containing fibers, filler particles or other particles produced by the layer-by-layer deposition of two interacting polymers, preferably anionic and cationic polyelectrolytes, which are typically used as dry and wet strength agents in the paper manufacture. Accordingly, this document also evaluates the tensile strength of the paper product.

WO 2005/032512 relates to an article comprising a particle, a first neutral polymer film and a second neutral polymer film which are associated by hydrogen bonding between a hydrogen bond donor polymer, such as polycarboxylic acid and a hydrogen bond acceptor polymer such as polyether, polyketone, polyaldehyde, polyacrylamide, polyamine, polyester, polyphosphazene or polysaccharide or a copolymer thereof. It is stated that capsules as one embodiment of this article are useful to deliver the core particle in a controlled and well-defined manner upon exposure to external stimuli. Application areas mentioned in this document are biotechnology, medicine, pharmaceuticals, foods, agriculture, perfumery, personal care and cosmetics.

US 2004/0137039 A1 provides in one embodiment a method of releasing low molecular weight polymers, such as drugs, dyes or other molecules from a LBL polymer film having a net excess charge, by introducing to the system at least one other type of molecule that binds reversibly to the film and thereby reduces the net excess charge. A second embodiment pertains to a method of selectively and reversibly releasing oligomeric and polymeric molecules, such as natural and synthetic polypeptides, oligo- and polynucleotides or other molecules having plurality of charges, from a LBL film formed from these oligomeric and polymeric molecules and a second polymer having the opposite charge, in response to variation in pH or ionic strength.

The controlled release of dyes from LBL films is also described in "A. A. Antipov et al., Sustained Release Properties of Polyelectrolyte Multilayer Capsules; J. Phys. Chem. B 2001, 105, 2281-2284" and mentioned in "M. Freemantle, Polyelectrolyte Multilayers; Science & Technology (2002), 44-48".

US 2004/0047979 A1 describes an improved layer-by-layer-coating process for modifying the surface of a medical device preferably an ophtelmic device, more preferably a contact lense. Polyanionic and polycationic polymers are employed for this layer-by-layer coating which is said to increase the hydrophilicity of a medical device.

U.S. Pat. No. 5,885,753 discloses a self-assembled multilayer that can be effectively produced from two or more self-assembled monolayers on a substrate where each of the self-assembled monolayers is produced for a block containing a first functional group and a second functional group reacting with each other. Polymerized mono- or multilayer embodiments thereof can be employed in a variety of applications including photolithography.

WO 2004/07677 A2 relates to a continuous process for manufacturing electrostatically self-assembled coatings. Under background of the invention it is explained that such multilayer assemblies have found use in applications for full color flat displays, membrane separation, barrier coatings, corrosion control coatings, electrochromic coatings, electroluminescent devices, conducting and insulating circuits, optical and non-linear optical devices, solar cells, high strength composites and multielement chemical sensors. According to preferred embodiments of this method, layers of polycationic polymers and negatively charged inorganic materials, such as platelet clays are arranged alternately in layers having a thickness of about 1 nm.

U.S. Pat. No. 6,428,811 B1 relates to a thermally sensitised polymer-particle composite that absorbs electromagnetic radiation and uses the absorbed energy to trigger the delivery of a chemical. Metal nanoshells are nanoparticulate materials that are suitable for use in these composites.

WO 00/63115 relates to multilayer carbon nanotube films.

U.S. Pat. No. 6,861,103 B2 relates to a method for forming organic thin films on a substrate surface, preferably a silicon waver surface.

On the other hand, there is also one document relating to multilayer construction in diapers. WO 2005/023536 discloses an absorbent article comprising at least one first microlayer film region having a liquid intake function, at least one second microlayer film region having a liquid uptake and distribution function, at least one third microlayer film region having a liquid retention function, and at least one fourth microlayer film region having a liquid barrier function. These first, second, third and fourth microlayer film regions are co-extruded and assembled with each other to form the unitary micro-layered film system. However, these layers apparently have a thickness above the nm range and do not assemble themselves.

Controlled release systems utilizing a homogeneous (not-layered) matrix are also known and frequently encountered in the medical area.

WO 97/04819, as one example of this technology, relates to a medical device for controlling a bacterial infection wherein said device comprises a pH-sensitive polymer matrix containing a biologically active agent, said agent being released from said polymer matrix upon pH change. This matrix is homogenous and is not obtained by layer-by-layer deposition of two interacting polymers. U.S. Pat. No. 5,607,417 discloses a medical device for controlling a bacterial infection of a similar type as described in WO 97/04819.

WO 2005/013906 discloses a pH-responsive film comprising (a) a biocompatible, hydrophilic polymer that is positively charged at a first pH and in electronically neutral form at higher pH; and (b) an alkylene oxide polymer or copolymer. The film is obtained by dissolving all components followed by solvent-evaporation film casting. It has a thickness of about 3 to 6 mil and can be used for contraception, treatment and/or prevention of viral infections, treatment of vaginal infections, relief of vaginal itch, vaginal cleansing and enhancement of vaginal lubrication.

OBJECTS AND SUMMARY

In view of the above, it is one technical object to provide an absorbent article with an economic carrier for active agents, in particular a controlled release system that shows the smallest possible effect on other properties of the substrate to which the carrier is applied.

Moreover, it is another technical object to provide an absorbent article with a carrier for active agents, in particular a controlled release system that is flexible and adapts to configuration changes of the underlying substrate.

It is one further technical object to provide an absorbent article with a carrier for active agents, in particular a controlled release system that is suitable for treating irregular surfaces, for instance fibers as used in many diaper products.

It is one further technical object to provide an absorbent article with a carrier for active agents, in particular a controlled release system that can be applied rapidly (e.g. by dipping, spraying, printing, coating, etc.) and uniformly.

It is one further technical object to provide an absorbent article with a carrier for active agents, in particular a controlled release system that can be manufactured without the aid of organic solvents or other environmentally undesired chemicals.

It is one further technical object to provide an absorbent article with a carrier for active agents, in particular a controlled release system that allows localizing and protecting the active agent.

According to one embodiment of the present disclosure, it is one further technical object to provide an absorbent article with a controlled release system that is capable of releasing the active agent under the influence of an appropriate trigger such as changes in pH, temperature or salt concentration.

An absorbent article such as a diaper, panty diaper, panty liner, sanitary napkin, or incontinence device, wherein at least one part of said absorbent article carries a film comprising at least one monomolecular layer of a polymer having a functional group and an active agent, in particular such an absorbent article wherein the film ("LBL film") is obtainable by layer-by-layer (LBL) deposition of at least a first polymer having a first functional group and a second polymer having a second functional group capable of interacting with the first functional group. (In the following, a reference to "LBL films" is intended to apply equally to "films" having only one monomolecular layer, if not stated otherwise.)

According to one further aspect, it is provided the use of a film obtainable by the layer-by-layer (LBL) deposition of at least one first polymer having a first functional group, in particular a polycationic polymer and a second polymer having a second functional group capable of interacting with the first functional group, in particular a polyanionic polymer for releasing an active agent contained in said film upon wetting of said film by body fluids.

The LBL films used are capable of binding an active agent incorporated therein or deposited thereon and in this manner act as a carrier for the active agent. According to one embodiment, the LBL film releases the active agent in a controlled fashion. "Controlled release" means that the active agent is not immediately released, but either gradually and/or preferably in response to an outer trigger. LBL films, specifically those based on polyelectrolytes of opposite charges or alternating hydrogen donor/acceptor polymers, are for instance capable of showing an excellent response to triggers associated with body fluids, such as changes in temperature, pH and salt concentration (ionic strength).

Economic use is made of the carrier polymers and the active agent since only very small amounts are needed for LBL film formation. Simultaneously, bulk properties of the substrate (e.g. diaper part) carrying the LBL film are not altered more than necessary. Specifically, important characteristics such as softness, flexibility, porosity or absorbency will not suffer to an undesired extent. A thickness of preferably below 1 μm provides the LBL film with the necessary flexibility to follow movements of the underlying substrate. The LBL technique used is moreover most suitable to treat irregular surfaces such as those of fibers frequently occurring in absorbent products.

Further, it is advantageous that LBL technology is water-based and allows the formation of coating films without the use of potentially hazardous organic solvents.

The LBL film used moreover binds the active agent to that part of the absorbent article where they are needed. This film may also exert a protecting function against undesired influences such as body fluid ingredients, or for instance during storage, against long-time exposure to air or higher temperature which may enhance undesired migration tendencies of certain active agents.

DETAILED DESCRIPTION OF THE PREFERRED EMBODIMENTS

As "absorbent article" we understand articles capable of absorbing body fluids such as urine, watery feces, female secretion or menstrual fluids. These absorbent articles include, but are not limited to diapers, panty diapers, panty liners, sanitary napkins or incontinence device (as used for instance for adults). In some absorbent products without absorbent layer, such as specific panty liners marketed by the present assignee under various trademarks in connection with the product name "Freshness everyday", the absorbent capacity of topsheet and backsheet is sufficient to absorb small amounts of female secretion.

Such absorbent articles preferably have a liquid-pervious topsheet which during use is facing the wearer's body. They further comprise a liquid-impervious backsheet, for instance a plastic film, a plastic-coated nonwoven or a hydrophobic nonwoven and preferably an absorbent layer (core) enclosed between the liquid-pervious topsheet and the liquid-impervious backsheet.

The part of the absorbent article carrying the film (preferably LBL film) is preferably selected from a topsheet, backsheet, layers arranged between topsheet and absorbent layer, such as acquisition/distribution layers, fibers or particles used for diaper manufacture such as cellulosic fluff pulp and/or superabsorbent particles or fibers, as typically used as material for the absorbent layer, a waistband and leg cuffs.

A suitable topsheet may be manufactured from a wide range of materials such as woven and nonwoven materials (e.g. a nonwoven web of fibers), polymeric materials such as apertured plastic films, e.g. apertured formed thermoplastic films and hydroformed thermpoplastic films; porous foams; reticulated foams; reticulated thermoplastic films; and thermoplastic scrims. Suitable woven and nonwoven materials can be comprised of natural fibers (e.g. wood or cotton fibers), synthetic fibers (e.g. polymeric fibers such as polyesters, polypropylene or polyethylene fibers) or from a combination of natural and synthetic fibers. When the topsheet comprises a nonwoven web, the web may be manufactured by a wide number of known techniques. For example, the web may be spun-bonded, carded, wet-laid, melt-blown, hydroentangled, combinations of the above or the like. It is preferred to make use of apertured plastic films (e.g. thermoplastic films) or nonwoven materials based on synthetic fibers, e.g. those made from polyethylene or polypropylene homo- or copolymers and polymer compositions based thereon.

If present, the at least one further layer existing between the absorbent layer and the topsheet may be made from hydrophobic and hydrophilic web or foam materials. As "web material" we understand coherent flat fiber-based structures of paper tissue, woven or nonwoven type. The nonwoven material may have the same features as described above for topsheets.

Specifically, the at least one further layer may contribute to fluid management, for instance in the form of at least one acquisition/distribution layer. Such structures are taught for instance by U.S. Pat. No. 5,558,655, EP 0 640 330 A1, EP 0 631 768 A1 or WO 95/01147.

"Foam materials" are also well known in the art and for instance describe in EP 0 878 481 A1 or EP 1 217 978 A1 in the name of the present assignee.

The absorbent layer which may be partially or totally surrounded by a core wrap may comprise any absorbent material that is generally compressible, conformable, non-irritating to the wearer's skin and capable of absorbing and retaining liquids such as urine and other body exudates.

The absorbent layer may comprise a wide variety of liquid-absorbent materials commonly used in disposable diapers and other absorbent articles such as comminuted wood pulp, which is generally referred to as air felt or fluff. Examples of other suitable absorbent materials include creped cellulose wadding; melt blown polymers, including co-form; chemically stiffened, modified or cross-linked cellulosic fibers; tissue, including tissue wraps and tissue laminates, absorbent foams, absorbent sponges, superabsorbent polymers (such as superabsorbent fibers), absorbent gelling materials, or any other known absorbent materials or combinations of materials. Examples of some combinations of suitable absorbent materials are fluff with absorbent gelling materials and/or superabsorbent polymers, and absorbent gelling materials and superabsorbent fibers etc.

The backsheet prevents the exudates absorbed by the absorbent layer and containing with the article from soiling other external articles that may contact the absorbent article, such as bed sheets and undergarments. In preferred embodiments, the backsheet is substantially impervious to liquids (e.g., urine) and comprises a laminate of a nonwoven and a thin plastic film such as a thermoplastic film having a thickness of about 0.012 mm to about 0.051 mm. Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the absorbent article while still preventing exudates from passing through the backsheet. Exemplary breathable materials may include materials such as woven webs, nonwoven webs, composite materials such as film-coated nonwoven webs, and microporous films.

Diapers (including panty diapers) preferably comprise leakage prevention means in the form of leg cuffs such as gasketing and/or barrier cuffs, which can carry a film (preferably LBL film).

Barrier leg cuffs are disposed adjacent each of the two longitudinal side edges of a diaper and have a proximal edge affixed adjacent to the longitudinal side edge and a distal edge unsecured to at least a portion of the absorbent articles. Elastically contractible gasketing cuffs are disposed adjacent each of the longitudinal side edges of an absorbent article, said gasketing cuffs extending laterally outward from said longitudinal side edges. Should exudates flow beyond the barrier cuffs, leakage prevention is further enhanced by the gasketing cuffs forming an additional liquid-impervious barrier around the leg or waist of the wearer. An example of suitable gasketing and barrier leg cuffs is disclosed in U.S. Pat. No. 4,695,278. Leg cuffs can be manufactured from the same materials as described above for topsheets. Preferably, nonwoven materials based on synthetic fibers are used.

To enhance the anchorage of the LBL film to hydrophobic diaper materials it may be preferred to treat them with a thin primer and/or subject the same to a surface modification step. It is preferred to use primer materials that are known to show a good adhesion to hydrophobic materials, but simultaneously can be employed in LBL technology. One preferred primer of this type is polyethyleneimine (PEI). PEI coating leads to a positive surface charge. Moreover, it can be preferred to admix the active agent, e.g. skin care actives to the aqueous primer solution.

Preferred surface modification techniques involve plasma or corona treatment as described for instance in WO 99/001099. Both techniques increase the hydrophilicity of nonwoven or film surfaces, preferably to molar oxygen/carbon ratio exceeding 0.19 as described in WO 99/01099. Plasma-treated materials which are suitable for use as liquid-permeable topsheets are also described in U.S. Pat. No. 4,743,494 and WO 94/28568, EP 0 483 858 A1 and U.S. Pat. No. 4,351,784. Since corona and plasma treatment tend to introduce negatively charged groups into the surface, it is preferred to use polycationic polymers as first layer in the following LBL deposition.

Any part of an absorbent article can carry the nanoscalar film. The part to be treated can be appropriately selected by a skilled person and primarily depends on the type of active agent to be used. Skin care agents as one example of active agents are preferably incorporated into parts of the absorbent article that contact the skin of the wearer. As far as diapers are concerned, these contact areas comprise for instance the waist band, the topsheet and gasketing and/or front barrier leg cuffs. Generally, it is preferred to apply skin care agents to the leg cuffs, if present, and/or the topsheet of an absorbent article. LBL films comprising odour-controlling agents can also be used in other parts of an absorbent article, for instance below the topsheet on or in an acquisition/distribution layer, on or in the absorbent layer, for instance as coating of fluff pulp or superabsorbent particles, or as backsheet coating on that side of a backsheet facing the wearer.

The LBL film can be present as continuous or discontinuous coating on the part of the absorbent article to be treated. "Discontinuous" coatings include the random or patterned deposition of LBL films. Especially printing techniques are suitable for the application of patterns.

The "LBL film" includes at least one monomolecular layer. "Monomolecular" means in line with the common understanding of this term in the art that the extension (thickness) of the layer essentially corresponds to a monomolecular coverage of the treated surface with polymer molecules.

The "LBL film" preferably has a thickness in the nanometer scale, i.e. below 1 µm. Higher thickness values (e.g. up to 5 or up to 3 µm) can be reached if the active agent is present as large particles as may be the case with biological material (bacterial cells or parts thereof, e.g. lactobacillus). Preferably, the LBL film has a thickness of less than 100 nm, more preferably less than 50 nm (e.g. less than 20 nm). The measurement is conducted after drying the freshly deposited films at a relative humidity of 50% at 20° C. until the film thickness has reached an equilibrium under these conditions. Preferably, ellipsometry is used for the measurement.

The LBL film may be composed of a single monomolecular layer comprising one polymer having a functional group and an active agent. This embodiment is of interest for low molecular weight organic active agents where one layer can provide the necessary embedding of the active agent.

Single layer films, however, are sometimes not capable of providing a uniform coating. To enjoy the full benefits, it is therefore preferred to provide an LBL film which is composed of two or more layers, more preferably 2 to 100 layers, in particular 3 to 50 layers (e.g. 4 to 20 layers).

These multilayer embodiments are obtainable by a layer-by-layer deposition of at least a first polymer having a first functional group and a second polymer having a second functional group capable of interacting with the first functional group. The expressions "first" and "second polymer" are not to be understood as limiting regarding the order of applying these polymers. Of course, it is equally possible to start with the deposition of the "second" polymer followed by a layer of the "first" polymer. Moreover, LBL films having more than two layers may be formed from one or more types of a "first" or "second polymer", respectively. To give an example, a multi-layer polyelectrolyte film does not require the use of the same polycationic or polyanionc polymer in the respective layers. Thus, two or more different polycationic and two or more different polyanionic polymers can be used for film formation. Finally, it is also possible to use mixtures of two or more polymers of the same kind in one layer.

This layer-by-layer (LBL) deposition technique is well known in the art of making multilayer thin films (please refer for instance to "G. Decher and J. B. Schlenoff (ed), Multilayer Thin Films, Sequential Assembly of Nanocomposite Materials, Wiley VCH 2003", incorporated by reference). In line with the LBL technique, the term "layer" is not to be understood in a strict sense of a material zone showing exclusively a two-dimensional extension and strict boundaries to the adjacent layer. Measurements have shown that LBL-deposited layers show a certain spread of for instance up to seven times the average layer thickness (preferably up to 4 times). In other words, a single monomolecular polymer layer may penetrate into the neighbouring layers.

Nonetheless, the layering structure of these nanoscalar films and their thickness can be confirmed by various analytical techniques including UV/Vis spectroscopy, ellipsometry, X-ray reflectometry, neutron reflectometry, in situ atomic microscopy (AFM), quartz crystal microbalance (QCM), surface force measurements and others described in "G. Decher and J. B. Schlenoff, Multilayer Thin Films". The preferred method for determining film thickness is ellipsometry.

It is preferred that the functional group of the first, second and possible further polymers is a polar group. As "functional group" we understand groups that are not solely based on carbon and hydrogen atoms. Preferred functional groups comprise at least one oxygen, nitrogen, sulfur, phosphor, silicon or metal atom.

The interaction between the first and second functional group is preferably based on electrostatic attraction, donor/acceptor interaction, hydrogen bonding or specific recognition, in particular specific chemical or biological recognition (e.g. streptavidinavidin). The polymers used for LBL deposition preferably have a weight average molecular weight of at least 10,000, preferably at least 50,000, in particular at least 100,000 (as for instance determined by light scattering). Generally, higher molecular weights seem to favor LBL deposition. There is no specific upper limit regarding the molecular weight even though, in view of the desired use of a fully water-based coating technology, the polymers preferably remain water-soluble.

According to one embodiment of the present disclosure, the first polymer is a neutral polymer comprising a hydrogen bond donor ("hydrogen bond donor polymer"). Hydrogen-bond donors are moieties that contain at least one hydrogen atom that can participate in hydrogen-bond formation and a more electronegative atom bound to the hydrogen atom. Examples of these moieties include, but are not limited to, O—H, N—H, P—H, and S—H. The moiety C—H can also be a hydrogen-bond donor if the carbon atom is bound to another atoms through a triple bond, if the carbon atom is bound through a double bond to O, or if the carbon atom is bound to at least two atoms selected from O, F, Cl, and Br. This first neutral polymer is preferably selected from polycarboxylic acid, such as polyacrylic acid (PAA) or polymethacrylic acid, a polynucleotide, a polymer of vinylnucleic acid, polyaminoacids such as polyglutamic acid and poly(E-N-carbobenzoxy-L-lysine), and polyalcohols such as poly(vinyl alcohol), and a copolymer thereof.

In this embodiment, the second polymer is preferably a neutral polymer comprising a hydrogen bond acceptor ("hydrogen bond acceptor polymer"). Hydrogen-bond acceptors are moieties that contain an atom more electronegative than hydrogen that can also contain a lone pair of electrons. Examples of such atoms include, but are not limited to N, O, F, Cl, Br, I, S, and P. Preferred examples of this hydrogen bond acceptor comprise a polyether, polyketone, a polyaldehyde, a polyacrylamide, other polyamides, a polyamine, a polyurethane, a polyester, a polyphosphazene or polysaccharide or copolymer thereof. Specific examples involve polyethylene oxide, poly-1,2-dimethyoxyethylene, poly(vinylmethyl ether), poly(vinylbenzo-18-crown-6), polyvinyl butyral, poly (N-vinyl-2-pyrrolidone), polyacrylamide (PAAm), poly-methacrylamide, poly(N-isopropylacrylamide), poly(4-amine)styrene, poly(cyclohexane-1,4-dimethylene terephthalate), polyhydroxy methyl acrylate, poly(bis(methylamino)phosphazene), poly(bis(methoxyethoxyethoxy) phosphazene, carboxymethyl cellulose or a copolymer thereof.

Hydrogen bond donor polymers comprising acidic functions such as PAA must be deposited under (typically acidic) conditions where the acidic groups exist in their non-ionized form and are therefore available for hydrogen bond formation. Similarly, hydrogen acceptor polymers comprising basic functions should be deposited under pH conditions where the hydrogen acceptor exists in its non-ionized form. This is also to be considered when selecting a suitable combination of hydrogen bond donor and hydrogen bond acceptor polymer. One suitable combination of hydrogen bond donor and acceptor polymer is for instance PAA/PAAm which can be deposited from their aqueous solution at a pH around 3.

LBL films based on at least two alternating layers of at least one hydrogen bond donor and at least one hydrogen bond acceptor polymer are particularly susceptible to pH changes. This property can be utilized in controlled release embodiments. If the LBL film is for instance deposited at a pH different from normal urine, contact with urine will enhance the release of the active agent (e.g. one comprising a hydrogen bond donor and/or acceptor moiety) incorporated therein. The pH difference between the pH at which the alternating at least two layers of at least one hydrogen bond donor and at least one hydrogen bond acceptor polymer are deposited to the pH range of normal urine (5.8 to 7.4) is preferably at least 0.5 pH units ($\leq 5.3$ or $\leq 7.9$), in particular at least 1 or at least 2 pH units with increasing preference.

According to one further embodiment of the disclosure, the first polymer is a polycationic polymer and the second polymer a polyanionic polymer. Weak or strong polyelectrolytes may be used in LBL deposition. In strong electrolytes such as polystyrene sulfonate, the ionisation is complete or almost complete and does not change appreciably with pH. In weak electrolytes such as polyacrylic acid, the charge density can be adjusted by changing pH. Depending on the purpose of the LBL layer, it can be preferred to use weak polyelectrolytes, which allow for a better fine tuning of film properties. Especially in controlled release systems it is preferred to use weak electrolytes. Preferred weak electrolytes have $pK_a$ values of about 2 to about 10 (measured at 20° C. with an aqueous solution of 1 weight % polyelectrolyte containing in addition 5 mmol NaCl). Literature values for PAA and PAH are incidentally about 5.0 and 9.0, respectively; "Multilayer Thin Films", page 134. These polyelectrolytes may be homopolymers or copolymers wherein only a certain percentage (for instance at least 50 mol %, or less than 50 mol %) of all polymer-forming units carry the cationic or anionic group (Even though this is not always mentioned in the following for the starting materials, anionic groups in polyanionic polymers will carry a corresponding number of hydrogen atoms and/or metal atoms and/or onium groups (e.g. ammonium) for reasons of charge neutrality. Moreover, basic groups will be referred to as cationic even though, strictly speaking, the addition of a protic acid is even required to develop the cationic charge. Accordingly, deposition must proceed under pH conditions where the anionic and the cationic charge is available for inter-layer bonding). The polyelectrolyte may also be selected from biologically active polymers (DNA, RNA, proteins, oligo- or polypeptides, enzymes, etc.), although controlled-release films not including these are preferred in view of the lower stability of biologically active polymers, their higher costs, possible side effects during contact with the skin and the difficulty to purify these polymers.

Preferred polycationic polymers are preferably selected from homo- or copolymers of at least one monomer comprising a functional group that includes a nitrogen atom which can be protonated. They can have linear or branched structures.

Cationic polyelectrolytes can be selected from a) cationic or cationically modified polysaccharides, such as cationic starch derivatives, cellulose derivatives, pectin, galactoglucommanan, chitin, chitosan or alginate;

b) a polyallylamine homo- or copolymer, optionally comprising modifier units (suitable modifier units of the polyallylamine are known for example from WO 00/31150), in particular polyallylamine hydrochloride (PAH);

c) polyethylenemine (PEI);

d) a polyvinylamine homo- or copolymer optionally comprising modifier units, e) poly(vinylpyridine) or poly(vinylpyridinium salt) homo- or copolymer, including their N-alkyl derivatives, f) polyvinylpyrrolidone homo- or copolymer, a polydiallyl-dialkyl, such as poly (N,N-diallyl-N,N-di-$C_1$-$C_4$-alkyl-ammonium halide) as shown in U.S. 2004/0047979 A1, in particular poly (N,N-diallyl-N,N-dimethylammonium chloride) (PDDA);

g) a homo- or copolymer of a quaternized di-$C_1$-$C_4$-alkyl-aminoethyl acrylate or methacrylate, for example a poly (2-hydroxy-3-methacryloylpropyl-tri-$C_1$-$C_2$-alkylammonium salt) homopolymer such as a poly(2-hydroxy-3-methacryloylpropyl trimethylammonium chloride), or a quaternized poly(2-dimethylaminoethyl methacrylate or a quaternized poly(vinylpyrrolidone-co-2-dimethylaminoethyl methacrylate)

h) a poly(vinylbenzyl-tri-$C_1$-$C_4$-alkylammonium salt), for example a poly(vinylbenzyltri-methylammoniumchloride), i) Polymers formed by reaction between ditertiary amines or secondary amines and dihaloalkanes, including a polymer of an aliphatic or araliphatic dihalide and an aliphatic N,N, N',N'-tetra-$C_1$-$C_4$-alkyl-alkylenediamine, for example a polymer of (a) propylene-1,3-dichloride or -dibromide or p-xylene dichloride or dibromide and (b) N,N,N',N'-tetramethyl-1,4-tetramethylene diamine, j) POLYQUAD® as disclosed in EP-A-456,467; or k) a polyaminoamide (PAMAM), for example a linear PAMAM or a PAMAM dendrimer such as an amino-terminated Starburst™ PAMAM dendrimer (Aldrich).

l) cationic acrylamide homo- or copolymers, and their modification products, such as poly(acrylamide-co-diallyldimethylammonium chloride) or glyoxal-acrylamide-resins;

m) polymers formed by polymerisation of N-(dialkylaminoalkyl)acrylamide monomers, n) condensation products between dicyandiamides, formaldehyde and ammonium salts, o) typical wet strength agents used in paper manufacture, such as urea-formaldehyde resins, melamine-formaldehyde resins, polyvinylamine, polyureide-formaldehyde resins, glyoxal-acrylamide resins and cationic materials obtained by the reaction of polyalkylene polyamines with polysaccharides such as starch and various natural gums, as well as 3-hydroxyazetidinium ion-containing resins, which are obtained by reacting nitrogen-containing compounds (e.g. ammonia, primary and secondary amine or N-containing polymers) with epichlorohydrine such as polyaminoamide-epichlorohydrine resins, polyamine-epichlorohydrine resins and aminopolymer-epichlorohydrine resins as for instance mentioned in U.S. Pat. No. 3,998,690.

Preferred polycationic polymers are cationic or cationically modified polysaccharides such as starch or cellulose derivatives, chitin, chitosan or alginate, polyallylamine homo- or copolymers, polyvinylamine homo- or copolymers or polyethylenemine.

Examples of suitable polyanionic polymers include, for example, a synthetic polymer, a biopolymer or modified biopolymer comprising carboxy, sulfo, sulfato, phosphono or phosphate groups or a mixture thereof, or a salt thereof. They can have linear or branched structures.

Examples of synthetic polyanionic polymers are: a linear polyacrylic acid (PAA), a branched polyacrylic acid, a polymethacrylic acid (PMA), a polyacrylic acid or polymethacrylic acid copolymer, a linear or branched polycyanoacrylate, a maleic or fumaric acid copolymer, a polyamido acid, a carboxy-terminated polymer of a diamine and a di- or polycarboxylic acid (e.g., carboxy-terminated Starburst™ PAMAM dendrimers from Aldrich). Examples of a branched polyacrylic acid include a Carbophil® or Carbopol® type from Goodrich Corp. Examples of a copolymer of acrylic or methacrylic acid include a copolymerization product of an acrylic or methacrylic acid with a vinyl monomer including, for example, acrylamide, N,N-dimethyl acrylamide or N-vinylpyrrolidone.

Examples of polymers with sulfo- or sulfato groups are poly(anetholesulfonic acid), poly(vinylsulfate) (PVS), poly(vinylsulfonic acid), poly(2-acrylamido-2-methylpropane-sulfonic acid) (poly-(AMPS)) or a poly(styrenesulfonic acid) (e.g. sodium poly(styrenesulfonate); PSS) and examples of polymers with phosphate or phosphonate groups involve an alkylene polyphosphate, an alkylene polyphosphonate, a carbohydrate polyphosphate or carbohydrate polyphosphonate (e.g., a teichoic acid).

Examples of polyanionic biopolymers or modified biopolymers are: hyaluronic acid, glycosaminoglycanes such as heparin or chondroitin sulfate, fucoidan, poly-aspartic acid, poly-glutamic acid, carboxymethyl cellulose, carboxymethyl dextrans, alginates, pectins, gellan, carboxyalkyl chitins, carboxymethyl chitosans, sulphated polysaccharides.

One further class of polyanionic polymers, which partially overlaps with polymers described above, are those often used as dry strength agents in paper manufacture. These include polycarboxylic acids and anhydrides such as anionic starch derivatives, (meth)acrylic acid-derived polymers and copolymers, maleic-anhydride-derived copolymers, vinyl copolymers of carboxylic acids and anionic cellulose derivatives. These can be further exemplified by polyacrylates, polymethacrylates, maleic anhydride-vinyl acetate polymers, polyvinylmethylether-maleic anhydride copolymers, methacrylic acid-acryl amide copolymers, isopropenyl acetate-maleic anhydride copolymers, itaconic acid-vinylacetate copolymers, alpha-methyl styrene-maleic anhydride copolymers, styrene-maleic anhydride copolymers, methyl methacrylate-maleic anhydride copolymers, acrylic acid-styrene copolymers, carboxymethyl cellulose, succinic half esters of cellulose, graft polymerised polyacrylate-polyssacharide copolymers, succinic half esters of starch and oxidation products of the above-listed polyssacharides. The carboxyalkylated polysaccharides include carboxymethyl cellulose (CMC), carboxymethyl hydroxycellulose (CMHEC), carboxymethyl hydroxypropylcellulose (CMHPC), carboxymethylguar (CMG), carboxymethylated locust bean gum, carboxymethyl starch and the like, and their alkali metal salts or ammonium salts.

Preferably, the polyanionic polymer is selected from homo- and copolymers of acrylic acid and anionic starch or cellulose derivatives such as CMC.

When selecting suitable combinations (and concentrations) of first and second polymers, such as polycationic and polyanionic polymers, the interaction of potential candidates can be tested in solution prior to carrying out the deposition if both film constituents are soluble in the same solvent. When both solutions are mixed and flocculation occurs it is a good sign that multilayer fabrication will be possible. Like a chemical reaction, the precise structure of each layer depends on a set of control parameters known to a skilled person, such as concentration, pH, adsorption times, ionic strength or temperature, but in general the processing window is rather broad.

LBL films, specifically those made from non-crosslinked polyelectrolytes, are known to be responsive to external stimuli such as changes in pH and salt concentration. In addition to a slight change in temperature, these are precisely the conditions occurring when body fluids such as urine or menstrual fluids are released. Due to the gradual decomposition of urea, the pH of urine is slowly increased to mildly alkaline conditions. Moreover, the salt concentration of urine (about 7 g/l NaCl plus other salts) is relatively high.

If for instance a film obtainable by the layer-by-layer (LBL) deposition of at least one polycationic and at least one polyanionic polymer and containing an active agent is wetted by body fluids, salt bridges between positively and negatively charged ions located on the corresponding polyanion and polycation chains open to form nanopores and enhance the release of said active agent. Swelling of the LBL film accompanies this process. To enhance the controlled release capacity of the LBL films, it is preferred to deposit the same under "no or low salt" conditions and/or at pH values differing from the pH of urine. "No or low salt" conditions means that the LBL film is deposited from aqueous solutions of the "first" and "second" polymer and optionally the active agent (which may be of salt type) containing no other salts such as NaCl or, if other salts are present, in a concentration below the salt concentration of urine. Preferred low salt conditions are less than 5 g/l, more preferably less than 3 g/l, in particular less than 1 g/l of these other salts. The pH difference to the pH range of normal urine (5.8 to 7.4) is preferably at least one pH unit ($\leq 4.8 \geq 8.4$), in particular at least 2, 3 or 4 pH units with increasing preference.

Although body fluids such as urine or menstrual fluids provide the necessary concentration of salt to penetrate into the film, it has been also found that even high salt concentrations do not completely dissociate the polyions within the multilayer. Therefore, the LBL film produced in accordance with present disclosure will still show the necessary cohesion and adhesion to the underlying diaper part preventing a complete wash off.

According to one embodiment, the LBL film having controlled release properties comprises alternating layers of at least one polycationic and polyanionic polymer and a (negatively or positively) charged active agent. The charged active agent may be selected from the examples given below. To incorporate the active agent into the LBL film the same can be added to the aqueous solution of the polycationic polymer and/or the aqueous solution of the polyanionic polymer. Deposition is then conducted under conditions enhancing the formation of individual polymer layers binding the active agent. Alternatively, the LBL film is deposited first followed by loading the LBL film with the active agent. The latter technique is described in "A. J. Chung and M. F. Rubner, Methods of Loading and releasing low molecular weight cationic molecules in weak polyelectrolyte mulitlayer films Langmuir 2002, 18, 1176-1183" for poly(acrylic acid) (PAA), poly(alylamine hydrochloride) (PAH) multilayer films and methylene blue dye as model system. This article and the references cited therein describe how the loading of active agents into LBL films and their controlled release can be enhanced. These principles are also applicable to the present invention. Accordingly, it is preferred to use weak polyelectrolytes. Moreover, these weak polyelectrolytes are preferably deposited under conditions where the polycationic polymer and/or the polyanionic polymer are only partially ionised to provide binding sites for the later loading step. In contrast thereto, fully ionised polyelectrolytes often form highly ionically "crosslinked" multilayers with little or no binding sides for charged active agents and less permeability in the loading step. If the weak polyelectrolyte (for instance PAA at pH 2.5) is only partially ionised, this results in a nonstoichiometric pairing of repeating units creating relatively thick and loopy layers which are susceptible to swelling. During the loading step, preferably at a pH higher than used for deposition, the remaining protonated anionic groups (COOH in the case of PAA) can act as binding site for the charged active agent. Analogously, the opposite conditions can be used for incorporating a negatively charged active agent into an LBL film providing basic binding sides. A buffered solution of the charged active agent allows generally for a fast and more uniform loading. The article by Chung and Rubner moreover confirms that contact with high ionic strength solutions is an excellent trigger for controlled release irrespective of the type of polycationic and polyanionic polymer used.

According to one further embodiment, the LBL film having controlled release properties comprises alternating layers of at least one hydrogen bond donor polymer and at least one hydrogen bond acceptor polymer and an active agent having at least one hydrogen bond donor moiety and/or at least one hydrogen bond acceptor moiety as defined before. Suitable active agents may be selected from the examples given below. To incorporate the active agent into the LBL film the same can be added to the aqueous solution of the hydrogen bond donor polymer and/or hydrogen acceptor polymer. Deposition is then conducted under conditions enhancing the formation of individual polymer layers binding the active agent. Alternatively, the LBL film is deposited first followed by loading the LBL film with the active agent.

As "active agent" we understand agents showing biological, pharmaceutical and/or cosmetic activity as well as agents that fulfil or contribute to specific functions of absorbent articles or parts thereof such as odour control (e.g. by bacteria or pH control), skin care, softness, absorbency, etc. The active agent is preferably selected from odour-controlling agents and skin care agents. The active agent may be organic (e.g. a single molecule, an organic particle or a biological system) or inorganic (e.g. a single molecule or particle). The active agent may carry a charge (cationic or anionic) and it may also comprise a hydrogen bond donor or hydrogen bond acceptor moiety as defined before. Such active agents can be selected from the following classes and individual examples.

The active agent may further correspond to the aforementioned first (e.g. polycationic) and/or second (e.g. polyanionic) polymer provided that the same shows activity (e.g. odour-control or skin care) in the sense of the present disclosure.

The odour-controlling agents are preferably selected from
(a) bacteriostatic or bactericidal agents,
(b) pH-control agents,
(c) odour-absorbing or adsorbing particles,
(d) odour-decomposing catalysts and
(e) odour-masking compounds.

Depending on the polymer used for deposition a skilled person can properly select a suitable agent from (a) to (e). These may in particular carry a charge (cationic or anionic) under deposition conditions and/or comprise a hydrogen bond donor or hydrogen bond acceptor moiety.

One technique to combat malodour in absorbent products is based on the use of (a) organic bacteriostatic or bactericidal agents (in the following referred to as "antibacterial"), which reduce the number of odour-forming bacteria. It should be stressed, however, that not only odour-controlling antibacterial agents can be used but also those showing antibacterial activity regardless of the intended odour control.

Non-limiting examples of antibacterial agents comprise triclosan, chitosan, quaternary ammonium compounds, biguanides, peroxides, antibiotics, antibacterial peptides or proteins, iodine or iodophores, other halogenated compounds, especially brominated compounds. Quaternary ammonium compounds can be specifically exemplified by those having one or two substituents selected from long-chain (e.g. C8 to C24) organic residues or benzyl, e.g. benzalkonium.

According to one embodiment, polymeric antibacterial agents are used. In line with this embodiment, the polymer is preferably an antibacterial polycationic polymer such as chitosan or a polymer having cationic antibacterial groups of the above-exemplified type (e.g. biguanide, quaternary ammonium compounds). Such antibacterial polymers are described for instance in WO 98/18330 and WO 01/17357. This antibacterial polymer is preferably provided as top layer on an underlaying LBL film terminated with a polyanionic polymer. Thereby, an efficient binding of antibacterial polymers is achieved.

Antibacterial agents also include antibacterial nanoparticles of metals, their oxides, salts, complexes, alloys and mixtures of these. Examples of such metals include silver, zinc, gold, aluminium, copper, platinum and palladium, silver being preferred. Throughout the present application, the term "nanoparticle" designates particles having an average size (diameter or longest axis in the case of non-spherical particles) in the nanometer range, that is below 1 µm, preferably below 100 nm, more preferably below 20 nm, even more preferably below 10 nm, for instance 1 to 5 nm.

According to one embodiment, antibacterial metal nanoparticles are incorporated into the LBL film by providing an LBL film based on alternating polyelectrolyte layers which include a "second polymer" having an anionic group, preferably a carboxy group as in acrylic acid homo- or copolymers (e.g. PAA). This LBL film is then treated with an aqueous solution of a water-soluble salt of the respective metal, for instance silver acetate, followed by removal of the treated LBL film from this solution and an optional rinsing step with water. In this manner, the metal ions, for instance silver ions will bind to the anionic groups. Depending on the metal used, this metal-treated LBL film may already show antibacterial properties. Bound silver ions are preferably converted to metallic silver nanoparticles by reducing the ionic silver in a hydrogen stream. On top of a metal-containing layer, as desired, further layers can be applied as protective coating, preferably again by LBL deposition.

Suitable conditions for incorporating metal ions into LBL films and the optional subsequent reduction with hydrogen are for instance described in "P. C. Wang, M. F. Rubner and R.

E. Cohen, Polyelectrolyte multilayer nanoreactors for preparing silver nanoparticle composites: Controlled metal concentration and nanoparticle size, Langmuir 2002, 18, 3370-3375" and "S. Joly, R. Kane, L. R. Radzilowski, T. Wang, A. Wu, R. E. Cohen, E. L. Thomas, M. F. Rubner, Langmuir 2000, 16, 1354-1359" and references cited therein. Preferably, a weak polyanionic polymer is deposited in alternating layers with a weak or strong polycationic polymer under conditions leading to partial ionisation of the polyanionic polymer. That is a fraction of the anionic groups (for instance carboxyl groups as in PAA) remains protonated. The acid protons can be subsequently exchanged for metal cations. Upon reduction, zero valent metal nanoparticles can be formed although this is not needed for most systems such as Ag+ to develop an antibacterial effect. This technique allows for the uniform and random distribution of metal ions or particles (for instance Ag particles) throughout the LBL film. Repeated exchange and reduction cycles can be used for achieving very high metal contents in the LBL film. On the other hand, depending on the metal used, very small amounts (e.g. at least $10^{-7}$ wt. %, at least $10^{-6}$ wt. %, at least $10^{-5}$ wt. %, at least $10^{-4}$ wt. %, based on a film that was dried as described before) may already suffice to develop a strong antibacterial effect. Even at very high metal contents (for instance up to 75 wt %) the LBL layer still prevents aggregation of nanoparticles which otherwise would be a problem. A particular advantage in view of the intended use in absorbent articles is the firm binding of the metal ions or metal nanoparticles in the polymer (LBL) layer. Accordingly, risks and problems associated with inhalation of nanoparticles or skin penetration by nanoparticles are minimized. Alternatively, the metal ions such as Ag ions are directly deposited from an aqueous solution comprising the polyelectrolyte polymer, preferably a polycationic polymer such as PEI as taught by WO 2005/058199. Thereby, alternating layers of polycationic polymer-metal ion/polyanionic polymer such as PEI-Ag+/PAA can be formed.

According to one further embodiment, an LBL film is provided on the basis of alternating polyelectrolytes wherein the polyelectrolyte polymer forming the outer layer has a functional group (e.g. a Lewis base containing sulfur, phosphor or nitrogen, such as SH) capable of binding directly to metal nanoparticles, such a silver nanoparticles. As desired, a protective coating of further layers may be coated on this metal nanoparticle layer, preferably again by LBL deposition.

According to one further embodiment, the antibacterial metal nanoparticles are deposited on the substrate prior to LBL deposition of alternating layers to fix the nanoparticles.

Odours may be classified as being acidic, basic or neutral.

Acidic and basic odours are preferably combated by pH control agents (b). However, we wish to emphasize that pH control agents exerting no odour control may also be used. pH control agents may for instance be included for maintaining a pH value (3 to 7) acceptable to human skin in and/or on the absorbent article. A suitable pH control agent thus slightly lowers the pH of urine and can be selected from physiologically acceptable, preferably buffering compounds. Therefore, the same compounds as discussed below in connection with odour control can be employed.

Control agents for acidic odour have a pH greater than 7 and typically include inorganic carbonates, bicarbonates, phosphates and sulfates. Control agents for basic odour have a pH of less than 7. They are preferably selected from acids having one, two or three carboxylic acid groups, optionally at least one hydroxy or oxo group and preferably 2 to 10 (e.g. 3 to 6) carbon atoms. Control agents for basic odour include compounds such as citric acid, lactic acid, tartaric, gluconic, levulinic, glycolic, succinic, malic, fumaric acid, acid phophate salts as well as boric acid and maleic acid. They can be provided as buffering solution by adding appropriate amounts of base (e.g. NaOH or $Na_2CO_3$) which are preferably adjusted to pH values of 4.5 to 6.0 as described in U.S. Pat. No. 3,704,034. Their odour control effect may at least partially be also based on their antibacterial and enzyme-inhibiting action. For instance, urease inhibitors represent one class of suitable pH control agents.

To incorporate pH control agents into the LBL film, the polymers constituting the same may be deposited from at least one aqueous solution already containing these pH control agents in dissolved form. Alternatively, the LBL film is loaded with the pH control agent after film formation by contacting the same with an aqueous solution containing the pH control agent under suitable conditions.

The pH control for basic odour may also be enhanced by the formation of LBL films comprising acidic polymers. The acidic polymers preferably represent partially neutralized weak polyanionic polymers and can be selected from the above exemplified polymer classes. Examples of these partially neutralized polyanionic polymers are partially neutralized polyacrylic acid or polycationic acid. The corresponding LBL films themselves are capable of exerting pH control, even in the absence of any other active agent.

It should be noted that, as a rule, acidic pH control agents also have a growth-inhibiting effect on undesired microorganism (bacteria) in the absorbent article. This follows for instance from WO 00/35502 in the name of the present applicant which discloses that, especially in the presence of lactic acid-producing bacteria, pH values of 3.5 to 5.5 after wetting are most effective in the control of undesired microorganisms and undesirable odours produced thereby.

The most commonly utilized odour-controlling agents are odour-absorbing or adsorbing particles (c) which are primarily used for controlling neutral odour and preferably have a pH of approximately 7. They can have negative or positive surface charges. Examples of these known types of compounds include activated carbons, clays, zeolites, silicas, starches and certain combinations thereof. Examples of such agents are described in EP 0348 979 A1, EP 0 510 619, WO 91/12029, WO 91/11977, WO 91/12030, WO 97/46188, WO 97/46190, WO 97/46192, WO 97/46193, WO 97/46195 and WO 97/46196.

Examples of odour-decomposing catalysts (d) comprise metal or metal oxide nanoparticles such as iron oxide, titanium dioxide, gold and platinum nanoparticles as well as enzymes such as hydrolases, oxidases, reductases, catalases, proteases and lipases. As known in the art, the numbers of (particularly active) corners and edges increases sharply with size reduction. Therefore, catalytic activity has already been observed for various nanoparticulate materials where the corresponding bulk material is inactive.

Odour-masking compounds (e) are typically of perfume type and can be appropriately selected by a skilled person depending on the odour to be masked. Odour-masking compounds include for instance those described on page 22 of WO 02/056841.

Skin care agents are capable of imparting cosmetic, therapeutic and/or protecting benefits to the skin of the user. They can be used to prevent, alleviate or heal dermatitis and may also have a skin-soothing, antiphlogistic (reduction of skin irritation), antimicrobial, antibacterial, antiviral, astringent, wound-healing, cell-regenerating, anti-inflammatory and/or anti-itch effect. Many skin care agents show several of these effects at the same time so that a clear allocation to one mode of action is often not possible.

Preferred skin care agents are based on naturally occurring active agents (mostly from vegetable sources), or mixtures thereof as occurring also in plant extracts. The phrase "naturally occurring active agents" also includes their synthetic analogues.

Skincare agents can include substances which adsorb or absorb irritating components in urine or excrements, for example clay minerals (bentonite, kaolin, montmorillonite, etc.), silicon oxide compounds (quartz, zeolites, water glass, etc.) or activated charcoal. The substances are advantageously activated to be more adsorbent by means of various treatments, for example with quaternary ammonium compounds.

Skincare agents can include enzyme inhibitors, for example, metal salts of iron or zinc, trace amounts of heavy metal ions such as copper or silver, ethylene diamine tetraacetic acid (EDTA), soybean trypsin inhibitor, lima bean protease inhibitor, maize protease inhibitor, stearyl glycyrrhetinate, glycerol triacetate, betaine compounds, sulphobetaine compounds, cholestyramine, p-guanidinobenzoates.

Skincare agents can include pH-regulating additives of the type described above in connection with odour control, for example, organic or inorganic acids such as adipic acid, ascorbic acid, benzoic acid, citric acid, malic acid, tartaric acid, lactic acid, phosphoric acid or hydrochloric acid, or buffers made for example from said acids with corresponding salts. They can also include polymeric acids, for example polyphosphoric acid or polyacrylic acid.

Skincare agents can also include additions of probiotic microorganisms, characterized by being antagonistic towards undesired microorganisms, e.g. urinary tract pathogens or skin infection pathogens. Examples of probiotic microorganisms which can be used are individual strains or mixtures of several strains of lactic acid-producing bacteria as taken from the species *Lactobacillus acidophilus, Lactobacillus curvatus, Lactobacillus plantarum* or *Lactococis lactis*. Many lactic acid producing bacteria such as those of the *Lactobacillus* family carry negative charges on the outer cell wall and are thus suitable for deposition with polycationic and polyanionic polymers.

Skincare agents can also include substances such as:
Anti-inflammatory agents and/or wound-healing protectants, e.g. acetylsalicylic acid, allantoin, azulen, alpha-bisabolol, flavonoids, glycyrrhizinic acid and salts thereof, (e.g. potassium, ammonium or zinc salt), ichthammol (Inotyol®), tannins, panthothenic acid and salts thereof, e.g. calcium panthotenate, dexpanthenol, β-glucan including CM-β-glucan.
Astringents (vasoconstrictors), for example TiO, ZnO (and other Zn compounds), aluminium acetate solution, aluminium tartrate solution (and other Al compounds).
Bactericidal or bacteriostatic agents, specifically those showing effectiveness against "bad smell"-causing bacteria such as farnesol.
Antimicrobial agents, for example amorolfin, antibiotics, bacitracin, benzalkonium chloride, benzetonium chloride, cetrimide, fusidic acid, gentian violet (methylrosaniline chloride), hexachlorophene, hexylresorcinol, imidazole derivataties (for example biphonazole, econazole, ketoconazole, chiotrimazole, miconazole), chlorhexidine, nystatin, povidone-iodine, terbinafin, triclosan, hydrogen peroxide or zinc oxide.
Antiviral agents, for example acyclovir, imiquimod, podophyllotoxin, podophilox, cidofovir, penciclovir, vidarabin, idoxuridine, trifluridine, tromantadine, lamivudine.
Anti-irritating substances such as PEG-soja sterol or PEG phytosterol, e.g. those of PEG 5, 10, 15, 20, 25, 30 or 40 type.
Natural fatty acids, especially essential and/or polyunsaturated fatty acids, such as linoleic acid or linolenic acid, or oils containing the same such as evening primrose oil, lingonberry seed oil, blackcurrent seed oil.
(Pro)vitamins or (pro)vitamin derivatives such as ascorbic acid (vitamin C), vitamin A compounds (e.g. retinol, retinyl acetate, retinyl palmitate, retinal, tretinoin and isotretinoin), panthenol (provitamin B5), tocopherol (vitamin E), e.g. tocopheroal acetate or tocopherol balm.
Natural plant extracts, or ingredients thereof, e.g. aloe vera, aloe barbadensis or aloe capensis extracts, algae extract, avocado sterols, grapeseed extract, extracts from *avena sativa* (oat), calendula, e.g. calendula officinalis, hamamelis, e.g. *hamamelis virginiana* (witch hazel), *salvia officinalis* (sage), *camelia sinensis*, chamomile, e.g. *chamomile recutita, echnicacea purpurea, melissa officinalis, mentha piperita*, olive, e.g. *oleo europeae*, rosemary extract, liquorice root extract containing 18-glycyrrhetinic, acid, lime tree extract containing quercetin and/or glyco-rutin, marigold extract (calendula oil), ginkgo leaf extract containing quercetin and rutin, horse chestnut containing quercetin and campherol, avocado oil, birch extract, arnica, extract of rose of Sharon or St. John's wort, teatree oil, cucumber, hops, or *hamamelis* extracts.
Yeast extract.
Skin care agents such as alpha-hydroxy acids (citric acid, tartaric acid, lactic acid, malic acid, etc.), betaine (trimethylglycine), ceramides, flavonoids, phytosphingosine, phytosterols, which are optionally ethoxylated (available from Henkel under the tradename "Generol"), hyaluronic acid, chitosan (acetylated chitin), milk protein (*Lactis proteinum*), polysaccharides, ubiquinone (coenzyme Q10), urea, squalane or squalene, dragosantanol, panthenol, anthocyanidins, preferably naturally occurring ones, and ethoxylated quaternary amines.

Skincare agents can also include glucocorticoids, preferably of low potency, for example hydrocortisone, or antipruritic, for example antihistamines or local anaesthetics (e.g. lidocaine). Depending on the type of polymer to be used for deposition, suitable skin care agents can be selected by a skilled person from the above classes, for instance those agents that carry a charge (cationic or anionic) under deposition conditions and/or comprise a hydrogen bond donor or hydrogen bond acceptor moiety.

Other examples of some different skincare agents and/or substances that can be used with the invention are described partially inter alia in the following documents: WO 96/16682 "Diaper having a lotioned topsheet~" (Roe et al.), WO 96/16681 "Diaper having a lotioned topsheet containing a polysiloxane emmollient" (Roe, Mackey), WO 97/05909 "Diaper having a lotioned topsheet comprising a liquid polyester emollient and an immobilizing agent" (Roe), WO 99/45973 "Disposable absorbent article having a skin care composition containing an enzyme inhibitor" (Roe et al.), WO 99/45974 "Protease inhibitors in absorbent products" (Rourke et al.), WO 99/45976 "Proton donating actives in absorbent articles" (McOsker et al.), DE 33 09 530 C1 "Hygienische Absorptionsvorlage" (Leitner et al.), DE 41 36 540 A1 "Einwegwindeln" (Grunecker et al.), U.S. Pat. No. 3,489,148 "Topsheet for disposable diapers" (Duncan et al.), WO 00/64502 "Absorbent article having a lotionized bodyside liner" (Krzysik et al.), WO 00/64501 "Skin-friendly absorbent articles and compositions" (Krzysik et al.), WO 00/64500 "Absorbent article having a hydrophilic lotionized bodyside liner" (Krzysik et al.), WO 00/64503 "Skin-friendly absorbent articles and compositions" (Krzysik et al.), WO 99/22684 "Web materials with two or more skin care compositions disposed thereon and articles made therefrom" (Roe et al.).

The absorbent article is manufactured by applying the LBL film on one part of this article. This part is preferably selected from a topsheet, a backsheet, fibers or particles as used for absorbent article manufacture, a waistband, gasketing and/or front barrier cuffs. The film can be applied to a part that can come in contact with the wearer's skin, such as a topsheet or leg cuffs if the active agent exerts beneficial effects on the skin of the user as is the case with skin care agents or pH control agents. Other active agents can be equally located in other parts of the absorbent article. The respective part of the absorbent article (e.g. diaper part) is then assembled in a known manner with the remaining elements of the absorbent article. Alternatively, the absorbent article or certain parts thereof are finalized prior to application of the LBL film.

One method for the manufacture of an absorbent article comprises in this order the steps of
(a) contacting one part of this absorbent article with a first aqueous solution of a first polymer comprising a first functional group to form a layer of the first polymer, followed by removing said first aqueous solution,
(b) optionally rinsing said part of the absorbent particle with water,
(c) contacting said part of this absorbent article with a second aqueous solution of a second polymer comprising a second functional group to form a layer of the second polymer followed by removing said second aqueous solution,
(d) optionally rinsing said part of the absorbent particle with water,
(e) optionally forming at least one further alternating layer in the same manner, wherein at least in one step the first or second aqueous solution also contains the active agent in dissolved or dispersed form.

The expression "contacting" covers all known coating techniques. These include the application of the aqueous solution by means of spraying, printing and roller coating and preferably by dipping the substrate into the aqueous solution.

As "aqueous solution" we understand solutions containing water as main solvent by volume, preferably in an amount of more than 50% by volume, more preferably in an amount of at least 80% by volume, in particular at least 90% by volume. The aqueous solution may also contain water-miscible organic solvents, such as water-miscible alcohols (e.g. methanol or ethanol), ethers (e.g. THF) or ketones (e.g. acetone). The inclusion of organic solvents can be utilized to control the deposition of the first and/or second polymer and thereby the layer thickness. Under certain conditions, mixtures of not more than 50 vol. % water and at least one water-miscible solvent may also be useful.

Alternatively to the above method, the active agent is deposited from a separate aqueous solution which is brought into contact with the substrate prior to the deposition of the first layer, or after the deposition of one, several or all layers of the LBL film, i.e. between any of steps (a) to (d), as part of the repetition cycle (e) or at the end of step (e).

According to one further technique for incorporating the active agent into the LBL film, the LBL film is formed in line with the above steps (a) to (e) before contacting the same with an aqueous dispersion or preferably solution of the active agent under conditions suitable for migration into the LBL film. Generally, changes in pH or ionic strength in the environment of the LBL film are used for increasing its permeability towards small molecules. This technique has been described in "A. J. Chung et al., Langmuir, 18, 1176 (2002)" and the example 1 of US 2004/0137039 with respect to poly (methacrylic acid)/polyethylene oxide LBL films and is for instance suitable for loading LBL films based on alternating polycationic and polyanionic polymers with charged active agents.

If the layer adjacent to the substrate is to be formed from the "second polymer", steps (a) and (c) have to be exchanged correspondingly.

Moreover, different types of a "first polymer" can be used in step (a) and the repeating sequence (e) and different types of a "second polymer" in step (c) and the repeating sequence (e).

Moreover, it is possible to fully omit at least one deposition step for one charged polymer (e.g. (a) or (c), or one of the depositions steps covered by the repeating sequence (e)) while replacing the same by the deposition of active agents such as particles, biological molecules (e.g. proteins) or systems (cells or cell fragments) having the same charge. This has been described in WO 2004/071677 for a negatively charged inorganic material having a thickness of less than about 10 nm. Useful inorganic material includes platelet clays that are easily exfoliated in aqueous solvent environments. The clays may be naturally occurring or synthetic. Platelet-shaped aluminosilicates can also be used for adsorbing malodours as upper or intermediate layer. Similarly, positively charged inorganic particles could be used for substituting at least one layer of a polycationic polymer.

One preferred biological system as replacement for one layer are bacterial cells for instance those of lactic acid-producing bacteria (e.g. *lactobacillus* and other families disclosed in WO 00/35502), fragments thereof, bacterial spores (especially *bacillus* spp.) as well as proteins, enzymes or antibodies.

There are no specific restrictions regarding the concentration of the first polymer in the first aqueous solution and the second polymer in the second aqueous solution. Preferably, the concentration ranges from 0.001 to 5 g/l, in particular 0.01 to 0.5 g/l. The active agent can be present in a similar concentration.

The layer deposition can be conducted in a relatively broad temperature range although, for reasons of convenience, film formation typically occurs at room temperature.

It should be understood that wherever features (materials, conditions, uses, etc.) are referred to as preferred, the disclosure of the present application also extends to combination of at least two of these features, as long as no contradiction arises thereby.

MORE PREFERRED EMBODIMENTS

The present disclosure is now illustrated by more preferred embodiments. These embodiments reflect a combination of features that are advantageously used.

Embodiment 1

A polyethylene-based nonwoven, preferably of the type as used for topsheet manufacture, is optionally subjected to corona discharge to create negative charges on the nonwoven surface. The (optionally corona-treated) nonwoven is dipped into an aqueous solution of an active ingredient or an aqueous solution comprising a mixture of an active ingredient and a primer polymer. Non-limiting examples of the active ingredient are skin care agents such as allantoin. Polyethylenimine (PEI) may be used as primer polymer. The active ingredient and the primer polymer form a first layer on the substrate.

The resulting nonwoven is then immersed alternately into aqueous solutions of polyacrylic acid (PAA) and poly(allylamine hydrochloride) (PAH) to deposit at least two coating layers. After each dipping step, the nonwoven is optionally rinsed with water. After the final deposition step the nonwoven is again optionally rinsed with water and then dried.

Embodiment 2

Cellulose fibers, for instance cellulose fibers as used in the manufacture of tissue layers or cellulosic fluff pulp as used in the manufacture of absorbent cores, are dipped into an aqueous solution of a cationic polymer, for instance the aforementioned wet strength agents. After draining and an optional rinsing step, the treated cellulose fibers are dipped into an aqueous solution of an anionic polymer, for instance the afore-mentioned dry strength agents, followed by draining the double-treated fibers and an optional rinsing step. This scheme can be repeated to deposit at least one further layer of the cationic and anionic polymer. After the deposition of a cationic layer, a layer of micro- or nanoporous zeolites is deposited on the fiber surface from an aqueous dispersion. The resulting zeolite layer can be protected from surrounding water and humidity in the air by depositing at least one further layer of cationic polymer and optionally at least one anionic polymer. Due to negative surface charges, the zeolite layer is thus capable of fully replacing one layer of anionic polymer. Instead of zeolite particles any other particle type having negative surface charges can be used.

Embodiment 3

Alternating layers of polycationic and polyanionic polymers are applied to a substrate material in the same manner as described in embodiment 1 and 2. The substrate material is for instance a topsheet (e.g. optionally corona-treated nonwoven or perforated plastic film) or a cellulosic material, for instance cellulose fluff pulp as used in the absorbent layer (optionally together with superabsorbent material) or acquisition/distribution layer. As final cationic layer, chitosan or modified chitosan is deposited from an aqueous solution to form an antibacterial film.

Embodiment 4

A substrate, preferably the absorbent layer of the absorbent article (e.g. those comprising cellulose fluff pulp and/or a superabsorbent material) or a neighbouring layer (e.g. tissue wrap or acquisition/distribution layer) is coated with at least two alternating layers of a polyanionic (e.g. PAA) and polycationic polymer (e.g. PAH) in any order from aqueous solutions of these polymers. Preferably, the polyanionic polymer is deposited under pH conditions leaving free acidic groups. Optionally, a rinsing step is conducted after each deposition. The resulting coated substrate is then immersed into an aqueous solution of a silver salt (e.g. acetate) to incorporate silver ions into the LBL film where they bind to the acidic groups. Although this is not required for antibacterial activity, the ionic silver atoms can be reduced in a hydrogen stream to metallic silver nanoparticles, which are bound in the polymer coating. One or more polymer layers can be applied as a protective coating as desired. If the final layer was of polyanionic type (PAA), the protective coating starts with a polycationic layer (PAH layer) optionally followed by at least one further layer fulfilling the alternating PAA/PAH construction principle. A more detailed description of suitable process conditions is found in the aforementioned references by Rubner (Langmuir 2000 and 2002).

This embodiment can be transferred to the incorporation of other metal ions or metal or metal oxide nanoparticles.

Although the present disclosure has been described with reference to certain preferred embodiments, it is apparent that modifications and variations thereof may be made by those skilled in the art without departing from the scope of the disclosure as defined by the following claims.

The invention claimed is:

1. An absorbent article, wherein at least one part of said absorbent article carries a film comprising at least one monomolecular layer of a polymer having a functional group and an active agent, and wherein the absorbent article is a diaper, panty diaper, panty liner, sanitary napkin or incontinence device, wherein the polymer has a pKa value of about 2 to about 10.

2. The absorbent article according to claim 1, wherein the film is obtained by layer-by-layer deposition of at least a first polymer having a first functional group and a second polymer having a second functional group capable of interacting with the first functional group.

3. The absorbent article according to claim 1, wherein the film is comprised of 2 or more layers.

4. The absorbent article according to claim 1, wherein the film has a thickness below 1 μm.

5. The absorbent article according to claim 1, wherein the functional group is selected from polar groups.

6. The absorbent article according to claim 2, wherein the interaction between the first functional group and the second functional group is selected from electrostatic attraction, donor/acceptor interaction, hydrogen bonding and specific recognition.

7. The absorbent article according to claim 1, wherein the active agent is an odour-controlling agent or a skin care agent.

8. The absorbent article according to claim 7, wherein the skin care agent is selected from naturally occurring active agents or mixtures thereof.

9. The absorbent article according to claim 7, wherein the odour-controlling agent is selected from bacteriostatic or bactericidal agents, pH control agents, odour-absorbing particles, odour-decomposing catalysts and odour-masking compounds.

10. The absorbent article according to claim 2, wherein the first polymer is a polycationic polymer and the second polymer is a polyanionic polymer.

11. The absorbent article according to claim 10, wherein the polycationic polymer is selected from cationic or cationically modified polysaccharides, polyallylamine homo- or copolymers, polyvinylamines homo- or copolymers and polyethylenemine.

12. The absorbent article according to claim 10, wherein the polyanionic polymer is selected from (meth)acrylic acid homo- or copolymers, anionic starch derivatives and anionic cellulose derivatives.

13. The absorbent article according to claim 10, wherein the film comprises at least one polycationic, at least one polyanionic polymer and a charged active agent.

14. The absorbent article according to claim 13, wherein the charged active agent is selected from the group consisting of odor controlling agents and skin care agents.

15. The absorbent article according to claim 2, wherein at least one layer is a layer of inorganic particles or other charged active agents.

16. The absorbent article according to claim 15, wherein the particles are selected from bacteriostatic or bactericidal metal particles, odour-decomposing metal particles and odour absorbing particles.

17. The absorbent article according to claim 2, wherein the film obtained by layer-by-layer deposition comprises at least one bacteriostatic or bactericidal polycationic polymer as an active agent, wherein the bacteriostatic or bactericidal polycationic polymer is present as an upper layer of said film.

18. The absorbent article according to claim 17, wherein the bacteriostatic or bactericidal polycationic polymer is chitosan.

19. The absorbent article according to claim 10, wherein the active agent comprises bacteriostatic or bactericidal metal ions or bacteriostatic or bactericidal metal particles dispersed through at least a part of the film.

20. The absorbent article according to claim 1, wherein the part comprising the film is selected from a topsheet, backsheet, layers arranged between topsheet and the absorbent layer, fibers or particles, a waistband and leg cuffs.

21. The absorbent article according to claim 20, wherein the absorbent article is a diaper or incontinence device and the part thereof carrying the film is selected from a topsheet, gasketing and/or front barrier cuffs.

22. The absorbent article according to claim 1, wherein the part is selected from a topsheet, gasketing or front barrier cuffs and is made from a hydrophobic material and is subjected to corona or plasma treatment prior to deposition of the film.

23. The absorbent article according to claim 14, wherein the part comprising the film is selected from a topsheet, backsheet, layers arranged between topsheet and the absorbent layer, fibers or particles, a waistband and leg cuffs.

* * * * *